(12) United States Patent
Dorfmüller et al.

(10) Patent No.: US 11,839,394 B2
(45) Date of Patent: Dec. 12, 2023

(54) REFLECTOR FOR ACOUSTIC PRESSURE WAVE HEAD

(71) Applicants: Medizinische Universität Innsbruck, Innsbruck (AT); Heart Regeneration Technologies GMBH, Innsbruck (AT)

(72) Inventors: Christian Dorfmüller, Rielasingen (DE); Johannes Holfeld, Innsbruck (AT); Michael Grimm, Vienna (AT)

(73) Assignees: Medizinische Universität Innsbruck, Innsbruck (AT); Heart Regeneration Technologies GMBH, Innsbruck (AT)

( * ) Notice: Subject to any disclaimer, the term of this patent is extended or adjusted under 35 U.S.C. 154(b) by 142 days.

(21) Appl. No.: 17/358,344

(22) Filed: Jun. 25, 2021

(65) Prior Publication Data

US 2021/0353320 A1 Nov. 18, 2021

Related U.S. Application Data

(62) Division of application No. 15/521,141, filed as application No. PCT/EP2015/074331 on Oct. 21, 2015, now Pat. No. 11,096,706.

(30) Foreign Application Priority Data

Oct. 21, 2014 (EP) ..................... 14189648

(51) Int. Cl.
*A61B 17/225* (2006.01)
*G10K 11/28* (2006.01)
*G10K 15/04* (2006.01)

(52) U.S. Cl.
CPC ............ *A61B 17/225* (2013.01); *G10K 11/28* (2013.01); *G10K 15/043* (2013.01)

(58) Field of Classification Search
None
See application file for complete search history.

(56) References Cited

U.S. PATENT DOCUMENTS 4,608,983 A 9/1986 Mueller et al.
4,702,249 A 10/1987 de la Fonteijne
(Continued)

FOREIGN PATENT DOCUMENTS

CN 103594081 B * 10/2018
DE 2538960 4/1977
(Continued)

OTHER PUBLICATIONS

Mittal et al., Soft Computing Research., IEEE, eNewsletter, 2009 Issue#29. This reference discloses the specific acoustic impedance of various materials on Table 1. (Year: 2009).*
(Continued)

*Primary Examiner* — Yi-Shan Yang
(74) *Attorney, Agent, or Firm* — Lewis & Reese, PLLC

(57) ABSTRACT

The present invention relates to a reflector for an acoustic shock or pressure wave head, wherein the reflector comprises an acoustically reflective surface formed by a body of rotation, said body of rotation being formed by rotation of an elliptical segment about a rotation axis which extends through a focal point of the ellipse and encloses an angle α between 0.1° and 30° with the main axis of the ellipse.

10 Claims, 8 Drawing Sheets

(56) References Cited

U.S. PATENT DOCUMENTS

| | | | | |
|---|---|---|---|---|
| 4,844,198 | A | * | 7/1989 | Ferralli .................. H04R 1/345 381/387 |
| 5,793,001 | A | | 8/1998 | Ferralli |
| 5,903,386 | A | * | 5/1999 | Mantravadi .......... G02B 19/009 359/853 |
| 6,036,661 | A | | 3/2000 | Schwarze et al. |
| 2005/0038361 | A1 | | 2/2005 | Zhong |
| 2008/0146971 | A1 | * | 6/2008 | Uebelacker ........ A61B 17/2251 601/4 |
| 2011/0034832 | A1 | * | 2/2011 | Cioanta ............ A61B 17/22029 601/1 |

FOREIGN PATENT DOCUMENTS

| | | |
|---|---|---|
| DE | 19718511 | 11/1998 |
| DE | 10065450 | 7/2002 |
| WO | 2011/006017 | 1/2011 |

OTHER PUBLICATIONS

International Search Report and Written Opinion regarding PCT Application No. PCT/EP2015/074331, dated Jan. 25, 2016.

Extended European Search Report regarding EP Application No. 14189648.0, dated Feb. 20, 2015.

Mittal et al., "Soft Computing Research," IEEE, eNewsletter, 2009 Issue #29, 2009.

Zhou et al., "The Effect of Reflector Geometry on the Acoustic Field and Bubble Dynamics Produced by an Electrohydraulic Shock Wave Lithotripter," J. Acoustic Sock Am. 2006, 119(6), 3625-3636, 2006.

Yang et al., "Deastigmatism and Circulatization of an Elliptical Gaussian Beam by Off-Axis Ellipsoid Reflector Based Off-Focus Configuration," Progress in Electromagnetics Research B, vol. 10, 91-103, 2008.

* cited by examiner

REFLECTOR FOR ACOUSTIC PRESSURE WAVE HEAD

FIELD OF THE INVENTION

The present invention relates to a reflector for an acoustic shock or pressure wave head and to an acoustic shock or pressure wave head with a reflector.

BACKGROUND

Acoustic shock or pressure waves have been used, e.g., in electrohydraulic lithotripsy to destroy hardened masses like kidney stones, bezoars or gallstones. An apparatus for generating pressure pulse/shockwaves is described, e.g., in U.S. Pat. No. 8,257,282. The apparatus comprises a pressure pulse/shockwave source, a housing enclosing said pressure pulse/shockwave source, and an exit window from which wave fronts of waves generated by said pressure pulse/shockwave source emanate. The wave fronts have plane, nearly plane, convergent off target or divergent characteristics. An extracorporeal shockwave system provides a planar wave for the treatment of tissue. A parabolic reflector is provided in order to propagate the planar wave through a membrane and to the tissue of a human subject.

A reflector having the shape of an ellipsoid is known from, e.g., U.S. Pat. No. 4,702,249. Further reflectors are known from, e.g., DE 197 18 511 A1, DE 253 89 60 C2 and DE 100 65 450 A1.

The techniques known in the prior art are all based on using either plane wave fronts or acoustic waves being focused into a small focal spot. However, while the use of a strongly focused wave may provide optimum results in case of lithotripsy, this is not the case with other medical applications such as, e.g., the application of acoustic waves to heart tissue during cardiac interventions. The application of shock wave to heart muscle needs to cover a certain area of the heart in order to treat the whole area affected by, e.g., an ischemia. Using focused shock waves, each pulse will only cover a small area and a lot of shock wave pulses would be necessary to cover the whole area. This would extend the treatment time and therefore the time the patient needs to stay under general anesthesia increasing the patient's risk for side effects due to anesthesia. On the other hand the use of plane wave fronts would cover a large area with each pulse but the energy flux density per pulse is limited due to the large area and the maximum energy output of the generator.

SUMMARY

It is an object of the present invention to provide an improved reflector for acoustic shock or pressure waves which may, inter alia, be utilized in such advanced medical applications.

Accordingly, the present invention relates to a reflector for an acoustic shock or pressure wave head. The reflector comprises an acoustically reflective surface formed by a body of rotation. Said body of rotation is formed by rotation of an elliptical segment (of an ellipse) about a rotation axis which extends through a focal point of the ellipse and encloses an angle α between 0.1° and 30° with the main axis of the ellipse.

The present invention is, inter alia, based on the idea to provide a reflector whose focal region is expanded or widened as compared to a focal spot achieved by prior art reflectors. It has been realized that the healing process of a diseased tissue area is, at least in part, started in healthy tissue which is provided at the edge or surrounding of the diseased tissue area. It is thus advantageous to use a focus region of maximum shock or pressure which provides sufficient acoustic pressure to said edges or surrounding of the diseased area. Preferably, said focus region has the shape of a ring, a biconcave rotational solid or a discus. Such focal regions, which deviate from the focal spots of prior art reflectors, may be achieved by adapting the various parameters of the body of rotation, which defines the acoustically reflective surface of the reflector.

Preferably, the short half-axis of the ellipse has a length between 10 mm and 300 mm, more preferably between 15 mm and 200 mm and particularly preferably between 20 mm and 100 mm.

Preferably, the ratio of the long half-axis to the short half-axis of the ellipse ranges between 1.05 and 2, more preferably between 1.1 and 1.9, and particularly preferably between 1.2 and 1.8.

Preferably, the following relationship is fulfilled for the length L of the short half-axis measured in mm and the angle α measured in degrees: $-0.003 \times L + 0.8 < \alpha < -0.1 \times L + 30$.

Preferably, the angle α is at least 1°, more preferably at least 3°, and particularly preferably at least 5°. Preferably, the angle is no larger than 20°, more preferably no larger than 15°, and particularly preferably no larger than 10°.

Preferably, the acoustically reflective surface comprises a material whose specific acoustic impedance is at least twice as large as the specific acoustic impedance of water. One preferred material is metal, e.g. brass or stainless steel.

According to another aspect of the present invention, a reflector for an acoustic shock or pressure wave head is provided, wherein the reflector comprises an acoustically reflective surface formed by a body of rotation, said body of rotation being formed by rotation of a parabola segment about a rotation axis which extends through a focal point of the parabola and encloses an angle α between 0.1° and 30° with the axis of the parabola.

Preferably, the reflector comprises an aperture wherein the following relationship is fulfilled for the aperture's radius R measured in mm and the angle α measured in degree: $-0.003 \times R + 0.8 < \alpha < -0.1 \times R + 30$.

Preferably, the angle α is at least 1°, more preferably at least 3°, and particularly preferably at least 5°. Preferably, the angle is no larger than 20°, more preferably no larger than 15°, and particularly preferably no larger than 10°.

Preferably, the acoustically reflective surface comprises a material whose specific acoustic impedance is at least twice as large as the specific acoustic impedance of water. One preferred material is metal, e.g. brass or stainless steel.

The present invention further relates to an acoustic shock or pressure wave head with a reflector according to any of the inventive aspects described above. The acoustic shock or pressure wave head comprises a source of acoustic shock or pressure waves, wherein said source is arranged in a focal point of the ellipse or the parabola.

Preferably, shock or pressure waves emitted by the source are reflected on the acoustically reflective surface such that a focus region of maximum shock or pressure is formed outside the shock or pressure wave head. Preferably, the focus region has the shape of a ring, a biconcave rotational solid or a discus. The optimum shape of the focus region may depend on the specific medical application the waves are used for. Since the present invention allows for a wide spectrum of focus regions the user of the inventive reflector or the medical practitioner may choose the proper shape of the focus region for each specific application.

Preferably, the focus region is defined by the fact that the shock or pressure within said focus region decreases no more than 4 dB, more preferably no more than 5 dB, particularly preferably no more than 6 dB with respect to the maximum value.

Preferably, the diameter of the ring, the biconcave rotational solid or the discus ranges between 5 mm and 30 mm, more preferably between 5 mm and 20 mm.

Preferably, the acoustic shock or pressure wave head further comprises a membrane which preferably has a specific acoustic impedance corresponding to the specific acoustic impedance of water. Preferably, the volume enclosed by the acoustically reflective surface and the membrane is at least partially filled with a liquid, preferably water. Preferably, the source comprises two electrodes for spark discharge. Preferably, the liquid is enriched with conductive, semiconductive or non-conductive particles.

The present invention further relates to a method of treating human tissue with an acoustic shock or pressure wave. The method comprises producing an acoustic shock or pressure wave by spark discharge between electrodes which are supplied with electrical current, said electrodes being provided in a liquid medium such as water. The method further comprises focusing the produced acoustic shock or pressure waves by means of a reflector as described above such that the focus region corresponds with a treatment region of the human tissue. Preferably, said method of treatment is electrohydraulic lithotripsy. Preferably, the human tissue being treated comprises one or a combination of the following tissues: heart tissue, muscle tissue, bone tissue, skin, tendons and ligaments, prostate tissue, kidney, pancreatic tissue, nerve tissue.

BRIEF DESCRIPTION OF THE DRAWINGS

Preferred embodiments of the present invention are further elucidated with reference to the following Figures.

DETAILED DESCRIPTION

Figure 1:
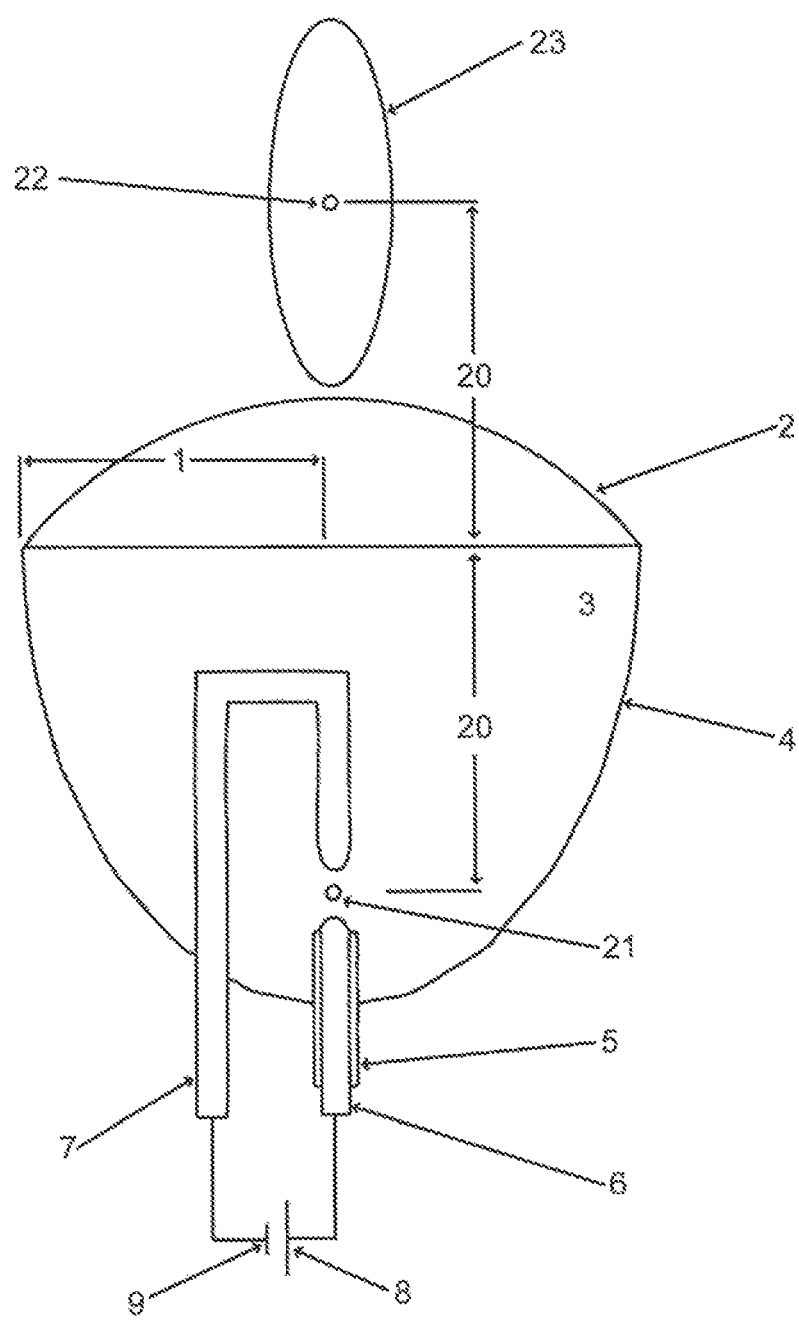
FIG. 1 shows a schematic cross-section of a reflector (including an electrode setup) according to the prior art.

FIG. 1 shows a schematic cross-section of a reflector for an acoustic shock or pressure wave head according to the prior art. The reflector comprises an acoustically reflective surface or reflector wall 4 in the shape of an ellipsoid (or, to be precise, a part thereof) with a first focal point 21 and a second focal point 22. The distance between the aperture of the reflector and each of the two focal points 21, 22 is indicated with reference numeral 20. The aperture radius is indicated with reference numeral 1.

The reflector shown in FIG. 1 may be part of an acoustic shock or pressure wave head comprising a source of acoustic shock or pressure waves. In case of FIG. 1, the source comprises two electrodes 6 and 7 connected to a source of high voltage 8, 9 with, e.g., the positive electrode 6 being electrically insulated from the reflector wall 4 by a high voltage isolator 5 and, e.g., the negative electrode 7 being either on the same potential as the reflector 4 or electrically insulated from it by another high voltage isolator (not shown). The source of acoustic shock or pressure waves is arranged in the first focal point 21. In other words, the tips of the electrodes 6 and 7 are provided on two opposing sides of the first focal point 21 so as to generate a spark at the very spot of the second focal point 21, if a high voltage is applied to the electrodes 6 and 7.

Figure 2:
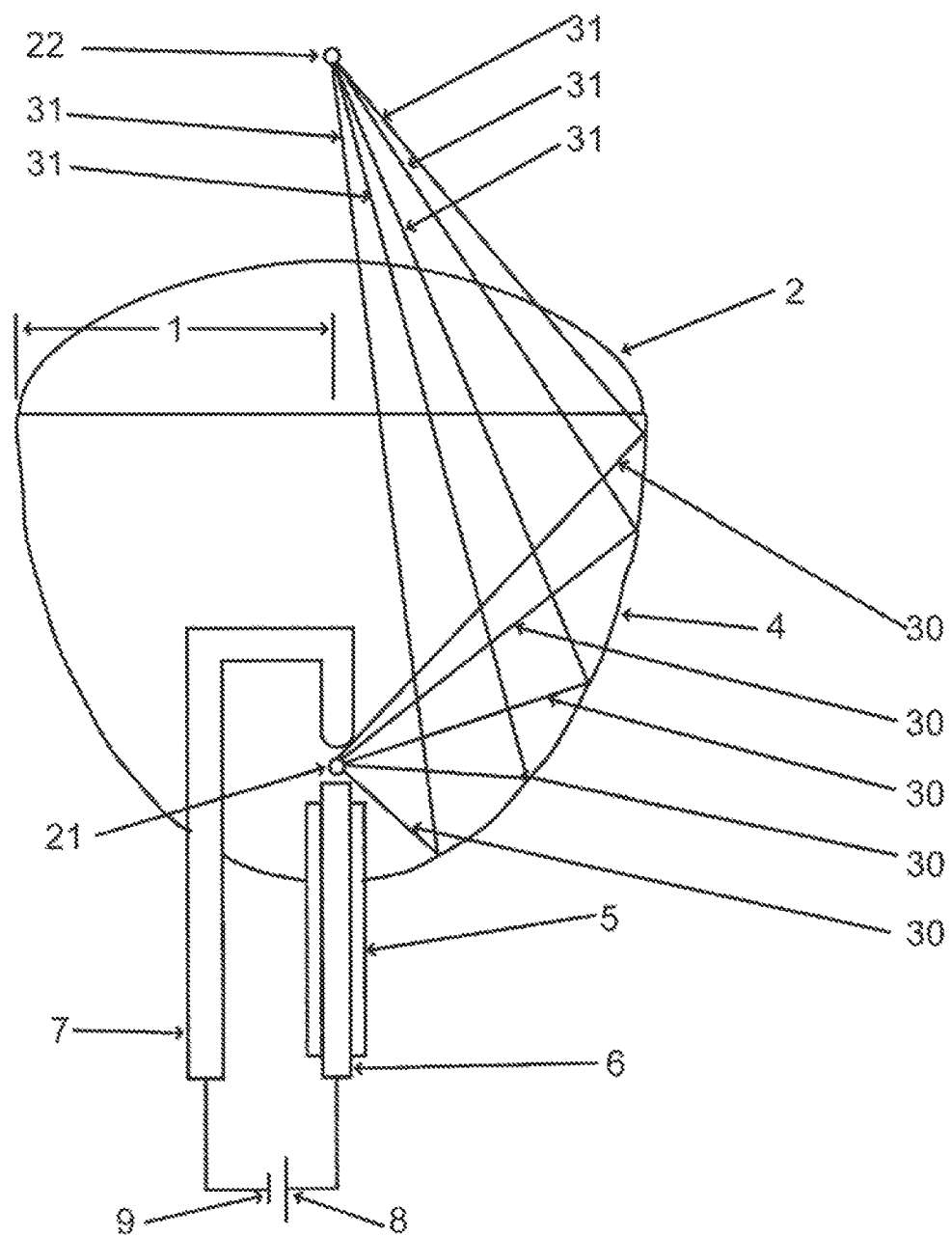
FIG. 2 shows a schematic cross-section of the reflector shown in FIG. 1 indicating the propagation of the acoustic waves.

The reflector volume 3, which is defined by the acoustically reflective surface or reflector wall 4 on the one hand, and a membrane 2 on the other hand is filled with a liquid such as water. The high voltage spark over generated at the first focal point 21 ionizes the surrounding water and thus generates a plasma which expands with supersonic speed. Thus, an acoustic shock or pressure wave is generated at the first focal point 21. The emitted pressure waves or beams 30 (see FIG. 2) travel through the water provided within the reflector volume 3 and are reflected at the acoustically reflective surface or reflector wall 4. The reflected acoustic waves or beams 31 are all focused in the second focal point 22 as shown in FIG. 2. The −6 dB focal region is indicated with reference numeral 23 in FIG. 1. As can be seen, the focal region 23 of this prior art reflector has roughly the shape of a prolate spheroid with the polar axis being substantially greater than the equatorial diameter.

Figure 3:
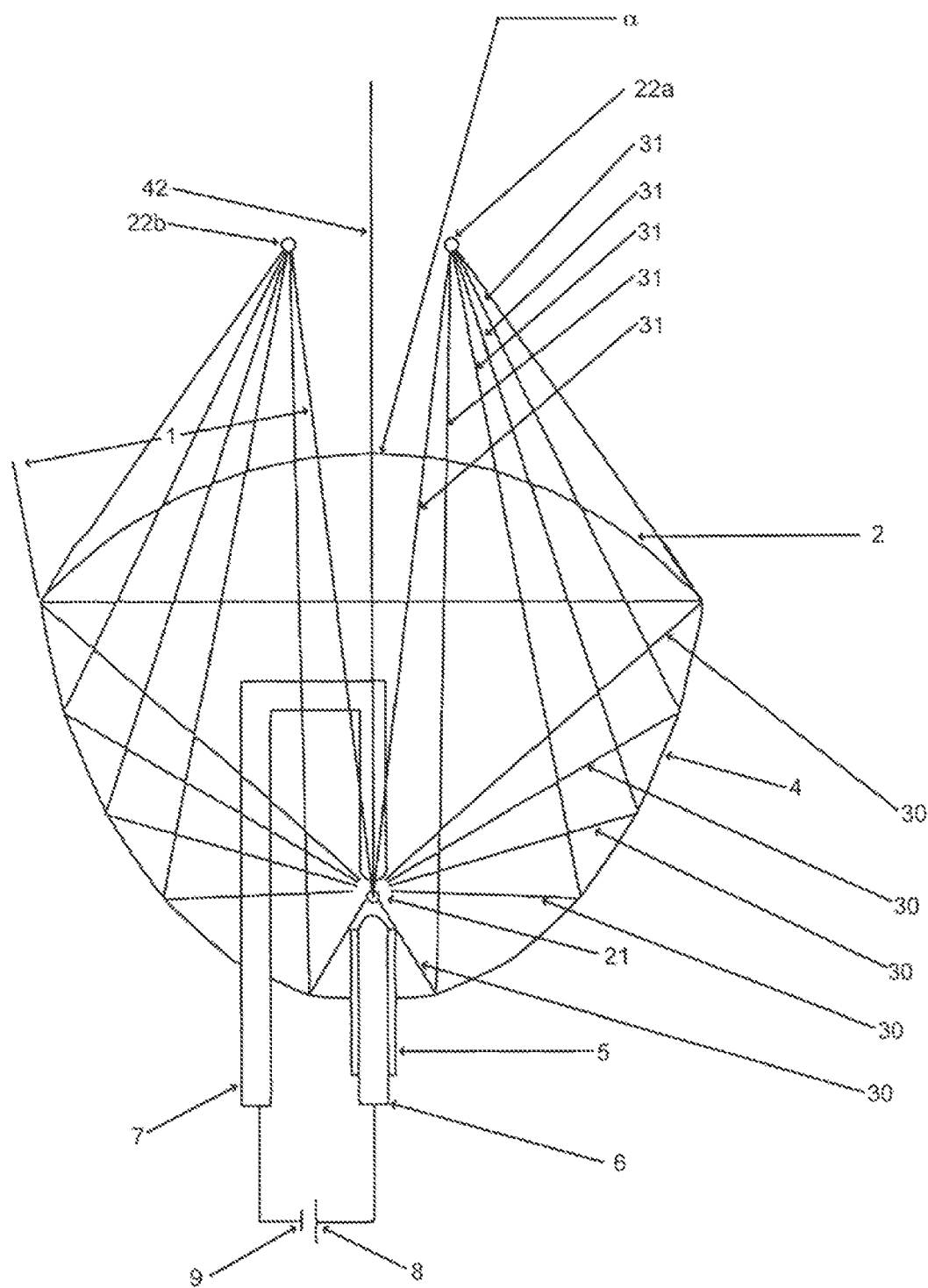
FIG. 3 shows a schematic cross-section of an acoustic reflector (including an electrode setup) according to a preferred embodiment of the present invention.

FIG. 3 shows a schematic cross-section of a preferred embodiment of a reflector for an acoustic shock or pressure wave head. The main components of the reflector including the electrode setup of the acoustic shock or pressure wave head are identical to those of the reflector shown in FIG. 1. However, while the acoustically reflective surface 4 of the reflector shown in FIG. 1 is formed by a regular ellipsoid (or a part thereof), the acoustically reflective surface 4 of the reflector shown in FIG. 3 is formed by a specific body of rotation. Said body of rotation is formed by rotation of an elliptical segment (of an ellipse) about a rotation axis which extends through a focal point of the ellipse and encloses an angle α with the main axis of the ellipse.

Figure 7:
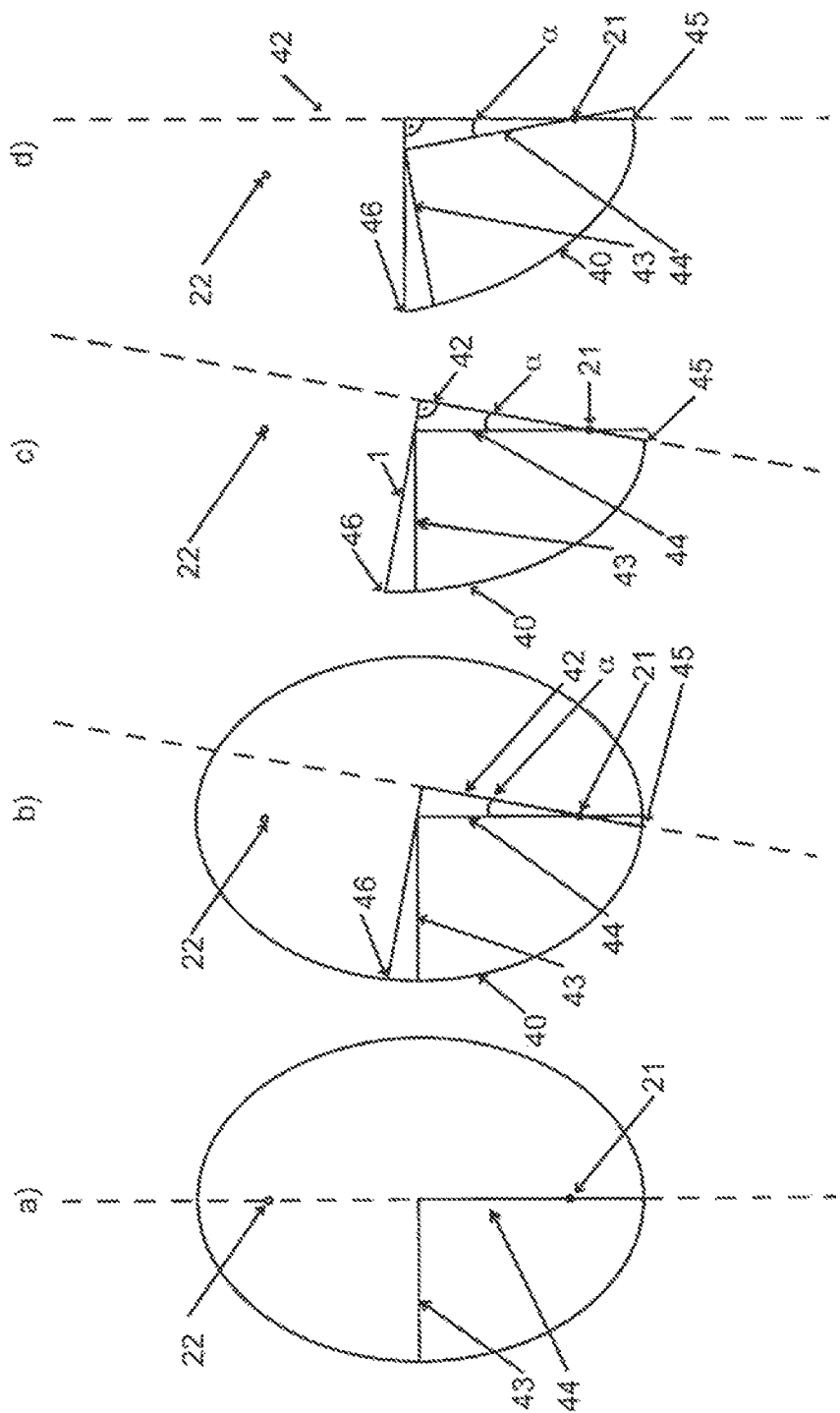
FIG. 7 shows a series of sketches indicating the generation of the body of rotation underlying the invention.

The formation of this body of rotation is schematically shown in FIG. 7. View a) shows an ellipse with first and second focal points 21 and 22, a short half-axis 43 and a long half-axis 44. The ellipsoidal reflective surface 4 shown in FIG. 1 would be achieved by rotation of the lower half of the ellipse shown in view a) about the main axis 44 of said ellipse. However, according to the present invention, the axis of rotation 42 encloses an angle α with the main axis 44 of the ellipse as shown in view b). As indicated in view c), a certain segment 40 of the ellipse is chosen, which segment is to be rotated about the axis of rotation 42. Said elliptical segment 40 need not correspond to exactly ¼ of an ellipse. Rather, a first end 45 of the elliptical segment 40 is preferably defined by the cross-section between the ellipse and the axis of rotation 42. The second end 46 of the elliptical segment 40 may extend beyond the cross-section of the short half-axis 43 with the ellipse as shown in view c). The perpendicular to the axis of rotation 42 extending through the second end 46 will later on correspond to the aperture radius 1 of the reflector. The elements of view c) are again shown in view d) with the axis of rotation 42 being now aligned with the vertical. Rotating the elliptical segment 40 about the rotation axis 42, which still extends through first focal point 21 of the ellipse underlying the elliptical segment 40 and which further encloses an angle α with the main axis 44 of the ellipse, will generate the acoustically reflective surface 4 shown in FIG. 3.

Due to the fact that the axis of rotation 42 and the main axis 44 of the elliptical segment enclose an angle, the second focal point 22 due to rotation about the axis of rotation 42 generates a ring-shaped focal region.

This is further explained with reference to FIG. 3, which schematically shows a cross-section through the acoustically reflective surface 4 formed by rotation of the elliptical segment 40 shown in view d) of FIG. 7 about the axis of rotation 42. Looking at the right-hand side of FIG. 3, it will be understood that each acoustic wave or beam 30 emitted from the first focal point 21 into the right-hand side of the cross-sectional plane of the reflective surface 4 is reflected into the second focal point 21a due to the fact that the first focal point 21 and the second focal point 22a are focal points of the elliptical segment forming the right-hand side of the cross-sectional plane of the reflective surface 4. Similarly, each acoustic beam 30 being emitted from the first focal point 21 into the left-hand side will be reflected onto second focal point 22b. Since this is true for each cross-sectional plane through the reflective surface 4, a focal region in the shape of a ring is being formed.

Figure 8:
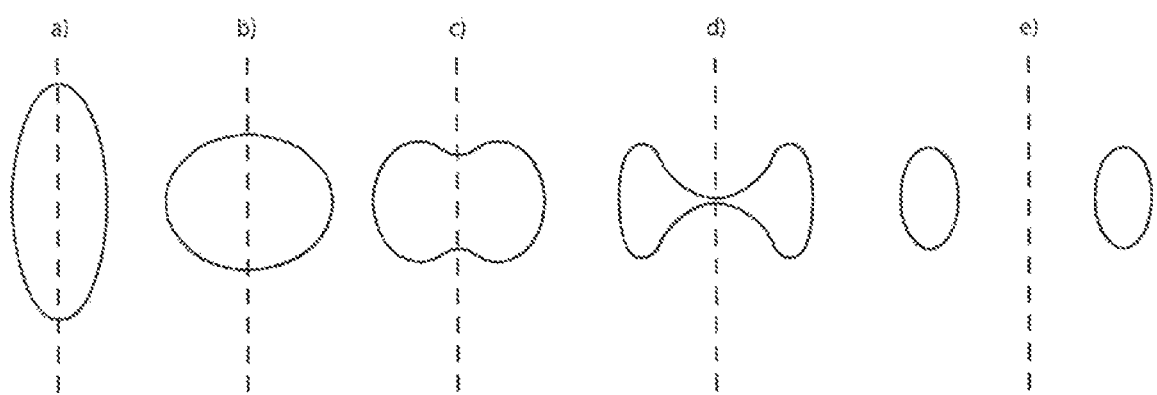
FIG. 8 shows schematic cross-sections through various focus regions.

Mathematically, the focal region of a regular ellipsoid should be a single point. Accordingly, the focal region of the reflector shown in FIG. 3 should correspond to a circular line. However, in real life, the point-like focus, due to imperfections, is expanded to the prolate spheroid shown in FIG. 1 (and, similarly, in view a) of FIG. 8) and the circle-like focal region of FIG. 3 is expanded to a toroidal or ring-like focal region as indicated in view e) of FIG. 8. Views a) to e) in FIG. 8 show the cross-sections of various focal zones or regions which may be generated by increasing the angle α enclosed by the axis of rotation and the main axis of the ellipse underlying the elliptical segment from view a) (α=0°) to view e). If the angle α is larger than 0° and preferably at least 0.1° the focal region shown in view a) is expanded or widened radially such that the prolate focal region shown in view a) becomes oblate as indicated in view b). Further increasing the angle α leads to a situation where the longitudinal extension of the focal region is greater at the periphery of the focal region than in the center of the focal region as can be seen in view c). At the same time, the maximum intensity of the pressure profile is off axis, i.e. displaced radially from the axis of rotation. The larger the angle α the further is the focal region expanded radially (see view d)) until, e.g., the −6 dB region forms a torus as shown in view e). Since the overall amount of energy or power transmitted does not change substantially, increasing the radial extension of the focal region at the same time reduces the longitudinal extension as schematically indicated in views a) to e) in FIG. 8.

Depending on the angle α and the particular profile of a single focal spot, the focal region can be manipulated to have the shape a discus as shown in view b) of FIG. 8, of a biconcave rotational solid as shown in views c) and d) of FIG. 8, or even of a torus as shown in view e) of FIG. 8.

As is evident from the above, the present invention allows for a very precise shaping of the focal region and, inter alia, provides the benefit of allowing for a focal region with a local minimum in terms of intensity and/or pressure at and/or close to the center of the focal region. A focal region as that shown in views c) to e) of FIG. 8 allows for a particularly beneficial treatment of diseased tissue, because treatment is focused or maximized at the edges or surrounding of the diseased tissue thus stimulating the at least partly healthy tissue around said diseased tissue. This specific shape adds a local pressure gradient between the two maxima of the focal zone occurring along a cross-section thereof. In views a) and b) of FIG. 8 the pressure gradient extends from the center of the focal zone radially to the periphery. In views c) to e) of FIG. 8 an additional pressure gradient occurs between the maximum pressure areas to the center of the focal zone and another one from the maximum to the periphery.

Figure 4:
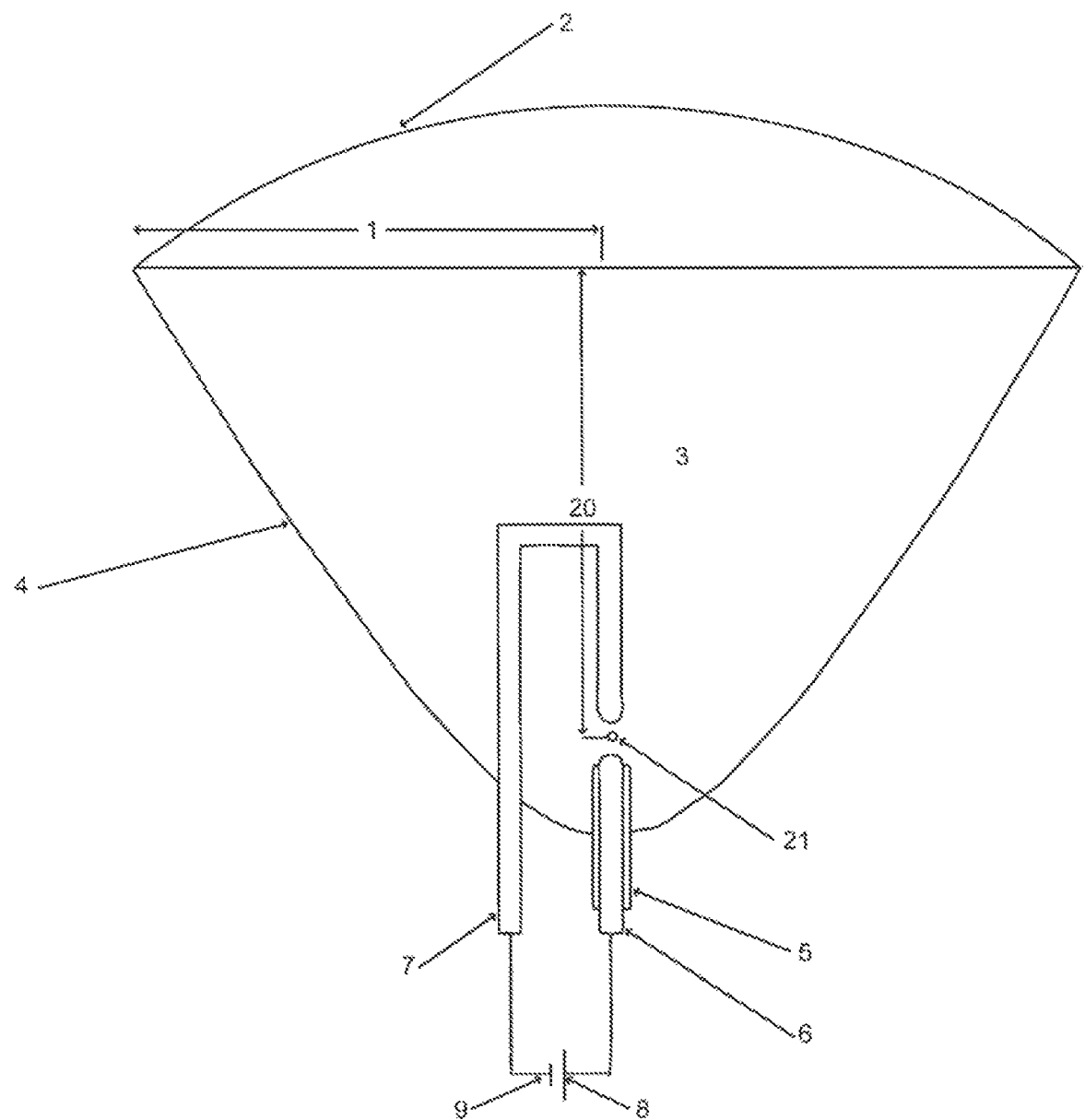
FIG. 4 shows a schematic cross-section of an acoustic reflector (including electrode setup) according to the prior art.
Figure 5:
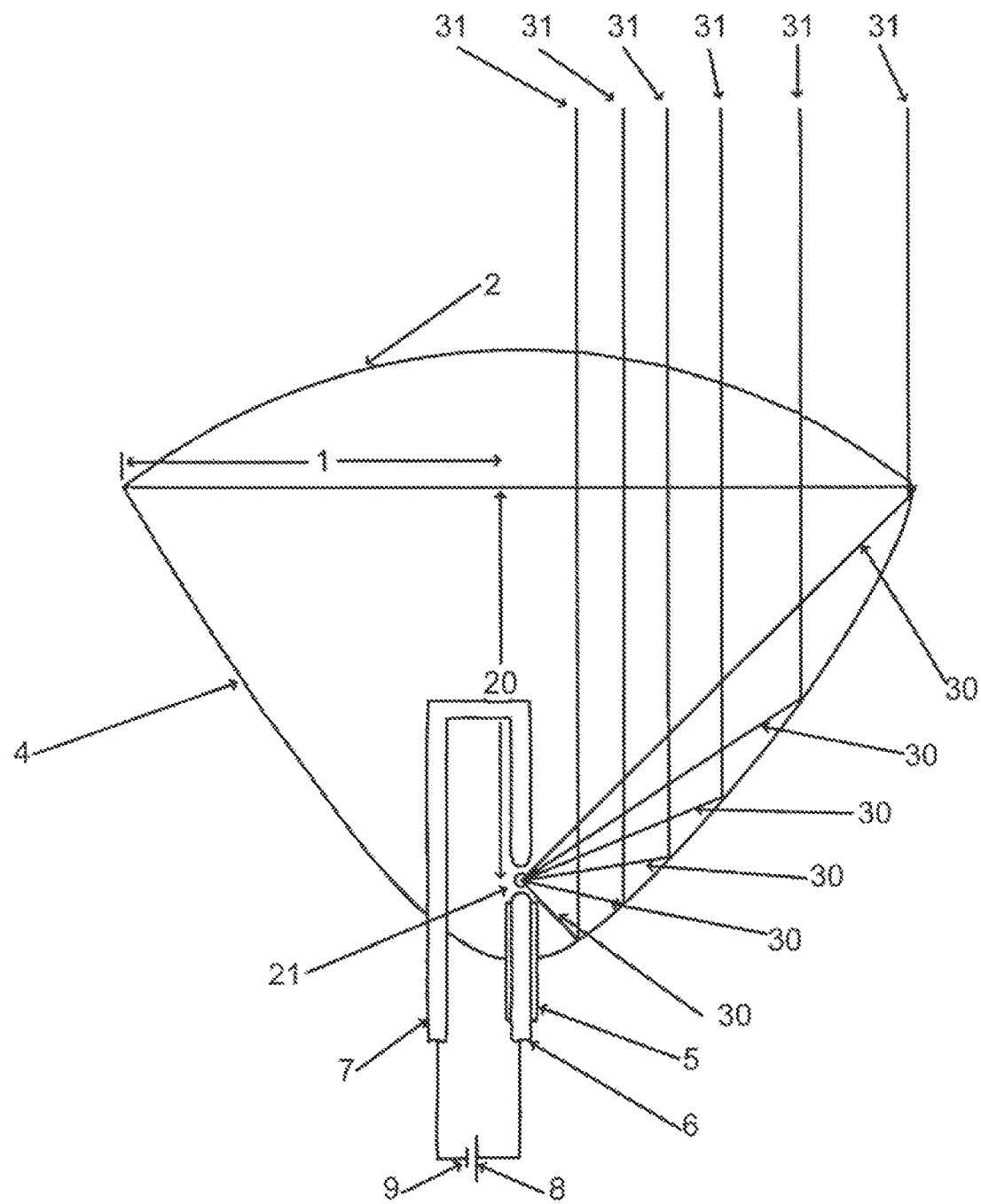
FIG. 5 shows a schematic cross-section of the acoustic reflector shown in FIG. 4 with the propagation of the acoustic waves being indicated.

FIGS. 4 and 5 show a schematic cross-section of another reflector known from the prior art, wherein the acoustically reflective surface 4 of said reflector has a paraboloid shape. Apart from the fact that a parabola only has a single focal point 21, the reflector shown in FIGS. 4 and 5 corresponds to that of FIG. 1. However, due to the parabolic shape of the acoustically reflective surface 4, the acoustic waves or beams 30 emitted from the focal point 21 lead to a plane wave of parallel reflected beams 31 as indicated in FIG. 5.

Figure 6:
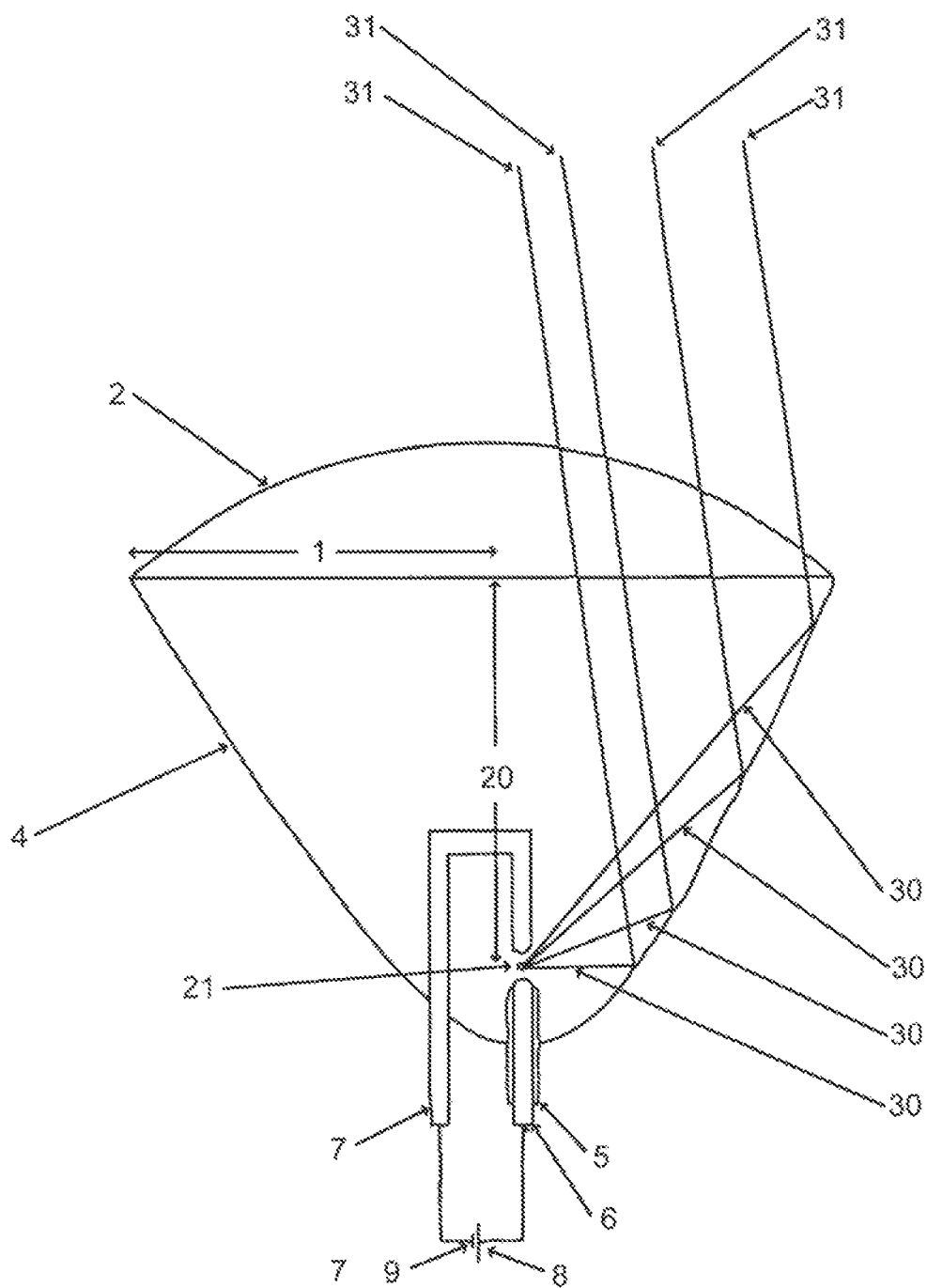
FIG. 6 shows a schematic cross-section of an acoustic reflector according to another preferred embodiment of the present invention.

FIG. 6 shows a schematic cross-section of another preferred embodiment of a reflector according to the present invention. Said reflector comprises an acoustically reflective surface 4 formed by a body of rotation. Similar to the body of rotation described above with respect to the elliptical segment, the body of rotation of the reflector shown in FIG. 6 is formed by rotation of a parabola segment about a rotation axis which extends through the focal point of the parabola and encloses an angle α with the axis of the parabola. The focus region achieved by the reflector shown in FIG. 6 is, in particular, discus-shaped, but may also have the shape of a ring or a biconcave rotational solid.

The reflector according to the present invention may be incorporated into any acoustic shock or pressure wave head known in the prior art. Even though the inventive reflector has been described with respect to reflection of acoustic shock or pressure waves, the invention may analogously be employed for reflection of other waves, in particular optical waves.

The invention claimed is:

1. A reflector for an acoustic shock or pressure wave head, wherein the reflector comprises an acoustically reflective surface formed by a body of rotation, said body of rotation being formed by rotation of a parabola segment of a parabola about a rotation axis which extends through a focal point of the parabola and encloses a tilting angle α between 0.1° and 30° from a main axis of the parabola.

2. The reflector according to claim 1, wherein the reflector comprises an aperture and wherein, dependent on the aperture's radius R measured in mm, the following applies for the angle a measured in degrees: −0.003×R+0.8<α<−0.1×R+30.

3. The reflector according to claim 2, wherein the angle a is no larger than 20°.

4. The reflector according to claim 1, wherein the acoustically reflective surface comprises a material whose specific acoustic impedance is at least twice as large as the specific acoustic impedance of water.

5. An acoustic shock or pressure wave head including the reflector according to claim 1, wherein the acoustic shock or pressure wave head further comprises a source of acoustic shock or pressure waves, wherein the source is arranged at the focal point of the parabola, wherein the acoustic shock or pressure waves emitted by the source are reflected on the acoustically reflective surface such that a focus region of maximum shock or pressure of the acoustic shock or pressure waves is formed outside the acoustic shock or pressure wave head.

6. The acoustic shock or pressure wave head according to claim 5, wherein the focus region has a shape of a ring, a biconcave rotational solid or a discus.

7. The acoustic shock or pressure wave head according to claim 5, wherein the focus region is defined such that a shock or pressure of the acoustic shock or pressure waves within said focus region decreases no more than 6 dB with respect to the maximum shock or pressure.

8. The acoustic shock or pressure wave head according to claim 5, further comprising a membrane, wherein a volume enclosed by the acoustically reflective surface and the membrane is at least partially filled with a liquid, and wherein the source comprises two electrodes for spark discharge.

9. The acoustic shock or pressure wave head according to claim 8, wherein the liquid is water.

10. The acoustic shock or pressure wave head according to claim 8, wherein the liquid is enriched with conductive, semiconductive or non-conductive particles.

* * * * *